US009933355B2

(12) United States Patent
Sawyers

(10) Patent No.: US 9,933,355 B2
(45) Date of Patent: Apr. 3, 2018

(54) MULTIPASS SPECTROSCOPIC ABSORPTION CELL

(71) Applicant: DUVAS TECHNOLOGIES LIMITED, London (GB)

(72) Inventor: Craig Sawyers, Oxford (GB)

(73) Assignee: DUVAS TECHNOLOGIES LIMITED, London (GB)

(*) Notice: Subject to any disclaimer, the term of this patent is extended or adjusted under 35 U.S.C. 154(b) by 0 days.

(21) Appl. No.: 14/911,202

(22) PCT Filed: Aug. 1, 2014

(86) PCT No.: PCT/GB2014/052372
§ 371 (c)(1),
(2) Date: Feb. 9, 2016

(87) PCT Pub. No.: WO2015/022494
PCT Pub. Date: Feb. 19, 2015

(65) Prior Publication Data
US 2016/0202175 A1 Jul. 14, 2016

(30) Foreign Application Priority Data
Aug. 14, 2013 (GB) .................. 1314571.9

(51) Int. Cl.
*G01J 3/44* (2006.01)
*G01N 21/03* (2006.01)
(Continued)

(52) U.S. Cl.
CPC ............ *G01N 21/031* (2013.01); *G01J 3/021* (2013.01); *G01N 21/33* (2013.01); *G02B 17/004* (2013.01);
(Continued)

(58) Field of Classification Search
CPC .. G01N 21/031; G01N 21/39; G01N 21/3504; G01N 2201/0636;
(Continued)

(56) References Cited

U.S. PATENT DOCUMENTS 2,779,230 A * 1/1957 White .................... G01N 21/65
356/301
4,626,078 A 12/1986 Chernin et al.
(Continued)

FOREIGN PATENT DOCUMENTS

| DE | 10308883 A1 | 9/2004 |
| JP | 2000-241313 | 9/2000 |
| WO | WO-01/46679 A1 | 6/2001 |

OTHER PUBLICATIONS

Combined Search and Exam Report under Sections 17 & 18(3) on GB1314571.9 dated Dec. 18, 2013.
(Continued)

*Primary Examiner* — Hoa Pham
(74) *Attorney, Agent, or Firm* — Christopher J. McKenna; Foley & Lardner LLP

(57) ABSTRACT

A multipass spectroscopic absorption cell comprises at least a first reflector (40) and a second reflector (42) that are configured to reflect a beam of light multiple times through a sample volume (V). At least one of the first and second reflectors (40,42) defines a principal optical axis (A) that extends through the sample volume (V). An optical folding system (52) is located on the principal optical axis (A) between the first and second reflectors, said optical folding system being configured to fold the principal optical axis (A) through an angle greater than 0°.

20 Claims, 6 Drawing Sheets

(51) Int. Cl.
*G01J 3/02* (2006.01)
*G01N 21/33* (2006.01)
*G02B 17/04* (2006.01)
*G02B 17/00* (2006.01)

(52) U.S. Cl.
CPC ....... *G02B 17/04* (2013.01); *G01N 2201/061* (2013.01); *G01N 2201/068* (2013.01); *G01N 2201/0636* (2013.01)

(58) Field of Classification Search
CPC ...... G01N 2201/0668; G01N 2021/391; G01J 3/42; G01J 3/14
USPC ......... 356/244, 246, 432–440, 318–319, 326
See application file for complete search history.

(56) References Cited

U.S. PATENT DOCUMENTS

| | | | |
|---|---|---|---|
| 4,953,976 A * | 9/1990 | Adler-Golden | G01N 21/65 356/301 |
| 5,065,025 A * | 11/1991 | Doyle | G01N 21/05 250/343 |
| 5,272,345 A | 12/1993 | Durham et al. | |
| 5,340,987 A * | 8/1994 | Eckles | G01N 21/3504 250/343 |
| 5,541,728 A * | 7/1996 | Dierking | G01J 3/4532 356/451 |
| 5,604,643 A | 2/1997 | Yamamoto | |
| 5,726,752 A * | 3/1998 | Uno | G01N 21/031 356/244 |
| 5,807,750 A | 9/1998 | Baum et al. | |
| 5,943,136 A * | 8/1999 | Pipino | G01J 3/42 356/439 |
| 6,201,245 B1 * | 3/2001 | Schrader | G01N 21/3504 250/343 |
| 6,486,474 B1 * | 11/2002 | Owen | G01N 21/031 250/339.02 |
| 6,979,088 B2 * | 12/2005 | Currie | G01N 21/031 359/529 |
| 2003/0227681 A1 | 12/2003 | Currie | |
| 2010/0201977 A1 * | 8/2010 | Milosevic | G01J 3/02 356/301 |
| 2010/0280315 A1 * | 11/2010 | Pan | A61B 5/0066 600/109 |
| 2010/0309454 A1 * | 12/2010 | Zhang | G01J 3/02 356/39 |
| 2013/0064259 A1 | 3/2013 | Wakabayashi et al. | |
| 2013/0130400 A1 | 5/2013 | Harbers et al. | |
| 2014/0291610 A1 | 10/2014 | Tseng et al. | |
| 2014/0334023 A1 | 11/2014 | Shi et al. | |
| 2015/0260695 A1 | 9/2015 | Spartz et al. | |
| 2016/0069797 A1 * | 3/2016 | Chanda | G01N 21/39 356/437 |
| 2017/0102315 A1 * | 4/2017 | Sawyers | G01N 21/031 |
| 2017/0139182 A1 * | 5/2017 | Sawyers | G01J 3/0264 |
| 2017/0139191 A1 * | 5/2017 | Paul | G02B 17/004 |

OTHER PUBLICATIONS

Examination Report under Section 18(3) on GB1314571.9 dated Apr. 15, 2016.
Examination Report under Section 18(3) on GB1314571.9 dated Nov. 12, 2015.
International Search Report and Written Opinion of the International Searching Authority on PCT/GB2014/052372 dated Oct. 15, 2014.
Ritz et al., "An Improved Open path Multi-Reflection Cell for the Measurement of NO2 and NO3", SPIE vol. 1715, Optical Methods in Atmospheric Chemistry, 1992, pp. 200-211.
International Search Report and Written Opinion for PCT/IB2016/056821 dated Feb. 1, 2017.
International Search Report and The Written Opinion for Application No. PCT/IB2016/055995 dated Mar. 29, 2017, 44 pages.
U.S. Office Action on U.S. Appl. No. 15/287,011 dated Oct. 6, 2017.

* cited by examiner

MULTIPASS SPECTROSCOPIC ABSORPTION CELL

CROSS-REFERENCE TO RELATED APPLICATIONS

This application is a U.S. national stage application under 35 U.S.C. § 371 of International Application No. PCT/GB2014/052372, filed Aug. 1, 2014, which claims the benefit of and priority to GB 1314571.9, filed Aug. 14, 2013, both of which are incorporated herein by reference in their entireties.

FIELD OF DISCLOSURE

The present invention relates to a multipass spectroscopic absorption cell and in particular but not exclusively to apparatus and methods for reducing the physical size and/or increasing the path length in chemical gas analysers based on multiple optical path absorption spectroscopy.

BACKGROUND

Optical absorption spectrometers are commonly used for gas phase absorption spectroscopy using the infrared, visible and ultraviolet parts of the optical spectrum (referred to collectively herein as "light").

The detection sensitivity of an optical absorption spectrometer depends on the interaction length, described by the de-Beer law.

The de-Beer law states:

$$P = P_0 \exp(-\sigma N I)$$

Where P is the transmitted optical power, $P_0$ is the incident optical power, $\sigma$ is the absorption cross section of the gas in $m^2$ per molecule (a characteristic of the gas), N is the gas concentration in molecules per $m^3$ and I is the interaction length (the length of gas that interacts with the light). This demonstrates that the absorption signal depends on the length of the gas column through which the light passes.

In order to maximise the interaction length in a cell of practical dimensions, there are a number of multiple pass optical designs which are based on sequential imaging of the optical beam using curved mirrors. The first multipass cell design was originally proposed and demonstrated by White (White, 1942) and is referred to generically as a White cell. This design is however rather sensitive to the optical alignment of the mirrors, typically measured in tens of microradians.

Later improvements, of relevance to infrared spectrometers, were introduced by White in which additional prisms were incorporated to increase the number of passes while reducing the mirror alignment sensitivity (White, ~1970's).

Alternative cell designs have been described by Herriott with the aim of producing a very high number of optical passes in the cell for use in infrared spectroscopy.

In a multipass cell the de-Beer law is modified as below:

$$P = P_0 \exp(-\sigma N K L)$$

Where L is the distance between the mirrors, and K is the number of optical passes.

Multipass cells as described above typically have a distance L in the range 400 mm to 1000 mm, and the number of optical passes K within the cell is typically in the range 12 to 500 passes. Thus the effective length over which the gas interacts with the light is typically in the range 4 meters to 500 meters.

The optimum number of passes K is a function of the optical losses in the cell. This is primarily related to the imperfect reflectivity of the mirrors. Multipass cells which operate in the infrared use very low loss mirrors having a reflectivity of about 99%, which allow a large number of passes. However, mirrors designed for use in the visible and ultraviolet (UV) regions of the spectrum have a lower reflectivity and hence much higher reflection losses, and this reduces the optimum number of passes. This is particularly a problem with UV mirrors, which typically have a reflection loss figure of greater than 10%, and it is also a smaller but significant problem with visible light mirrors.

Thus, multipass cells which operate in the UV (typically 150 nm to 400 nm) and visible (typically 400 nm to 700 nm) regions of the optical spectrum typically operate with 12 to 50 optical passes.

To summarise:

| Spectral region | Mirrors | Optimum Number of passes | Lamp used |
| --- | --- | --- | --- |
| UV | Enhanced aluminium | 12 to 40 | Deuterium |
| Visible | Enhanced aluminium or dielectric | 28 to 50 | Tungsten |
| IR | Gold | 50 to 1000 | Diode laser |

Typically multipass optical cells are incorporated into a measurement instrument. Additional subsystems are necessary to make such an instrument work satisfactorily. A suitable light source with associated collimation optical system is necessary to illuminate the multipass optical cell. The light source is preferably a continuous broadband light source, typically for example a Xenon arc lamp. Light exiting the cell is focused on the entrance slit of a spectrometer to provide an electrical signal characteristic of the fingerprint absorption spectrum of the gasses in the cell. An electronics subsystem running suitable algorithms carries out analysis of the spectrum in order to provide a measurement of the concentrations of gases in the cell.

Having arrived at the optimum number of passes, the only way in which the sensitivity of the instrument can be increased is to increase the cell length.

However, this gives rise to a design conflict. Since an optical cell is a simple structural element, the bending stiffness is proportional to the $1/(\text{cell length})^3$. Thus, for example, doubling the cell length to improve the detection sensitivity by a factor of two reduces the cell stiffness by a factor of eight, to the detriment of the long term stability of the instrument.

Furthermore, the longer the cell and/or the higher the optimum number of passes, the more difficult it is to align the optics. Generally doubling the cell length halves the allowable mirror misalignment. Likewise doubling the number of passes halves the allowable mirror alignment.

It would therefore be desirable to be able to increase the path length without increasing the cell length. However, in a conventional multipass cell this cannot be achieved without increasing the number of passes, which is prevented by the imperfect reflectivity of the mirrors particularly when operating in the infrared and also to a lesser degree when using visible light.

It is an aim of this invention to mitigate one or more the above problems.

U.S. Pat. No. 5,943,136 describes an optical cavity resonator device that is designed for measuring optical absorption using a high-Q optical resonant cavity. The device uses total internal reflection to generate an evanescent wave that decays exponentially at a point external to the cavity. Absorbing materials placed outside the cavity in the vicinity of this evanescent wave alter the Q-factor of the cavity, thus allowing the material to be probed. The device operates in entirely different way to the multipass spectroscopic absorption cell described herein, as the sample gas is not contained within the optical cavity. The patent is therefore mentioned here only for background interest.

SUMMARY

According to one aspect of the present invention there is provided a multipass spectroscopic absorption cell comprising a measuring chamber having a sample volume for receiving a sample gas, at least a first reflector and a second reflector that are configured to reflect a beam of light multiple times through the sample volume, at least one of said first and second reflectors defining a principal optical axis that extends through the sample volume, and an optical folding system located on the principal optical axis between the first and second reflectors, wherein said optical folding system comprises one or more prisms and is configured to fold the principal optical axis through an angle greater than 0°.

Folding the principal optical axis allows the length of the absorption cell to be reduced without reducing the pathlength or increasing the number of passes, thereby increasing the strength of the cell and significantly reducing alignment problems, while also making the cell more compact and portable. For example, in a UV multipass cell an interaction path length of up to 40 m can be achieved using a cell that is only 50 cm long, by folding the optical axis just once through 180°, whereas in a conventional instrument the cell would have to twice as long.

Alternatively, the invention allows the interaction path length to be increased without increasing the number of passes or the length of the absorption cell, thus increasing the sensitivity of the device. Thus, for example, in a UV multipass cell an interaction path length of up to 80 m can be achieved using a cell that is only 100 cm long, by folding the optical axis just once through 180°.

The use of prisms makes it possible to fold the principal optical axis without significantly increasing losses within the measurement cell. This is because a prism used in total internal reflection can have a transmission loss that is close to zero. This is particularly advantageous in an instrument that uses ultraviolet light (where the optimum number of passes is restricted to a relatively low number by the transmission losses of the mirrors), and also to a lesser degree when using visible light.

Advantageously, the optical folding system is configured to fold the principal optical axis at least once through an angle of approximately 180°. The optical principal optical axis is thus doubled back on itself, effectively halving the length of the cell. The principal optical axis is thus folded into two substantially parallel parts. An angle of approximately 180° is preferred as this allows the length of the cell to be reduced without increasing its width more than necessary. However, an angle less than 180° (for example in the range 170° to 180°) can also be used.

Optionally, the optical folding system may be configured to fold the principal optical axis twice through an angle of approximately 180°, thus folding the principal optical axis into three substantially parallel parts. This reduces the length of the cell to one third of its unfolded length and enhances still further the advantages mentioned above.

In a preferred embodiment the folded principal optical axis comprises a first part on a first side of the optical folding system and a second part on a second side of the optical folding system, and the optical folding system is configured to displace the first part from the second part by a displacement distance D, where D is greater than 0. Displacing the first and second parts of the principal optical axis ensures that the beam of light passes through different parts of the sample volume, thereby increasing the sensitivity of the device.

The optical folding system may comprise at least two prisms, wherein each said prism is configured to fold the principal optical axis through an angle of approximately 90°. Alternatively, the optical folding system may comprise at least one prism that is configured to fold the principal optical axis through an angle of approximately 180°.

Advantageously, each prism is made of a low loss material to provide a transmission loss of less than 1% with the chosen light. For example, the absorption cell may be configured for use with ultraviolet light and each said prism may be made of UV grade fused silica, which provides a transmission loss with UV of less than 0.1%. Alternatively, the absorption cell may be configured for use with visible light and each said prism may be made BK7 (borosilicate crown) glass, for very low transmission losses with visible light.

Advantageously, each prism includes at least one transmission face and at least one reflection face, the at least one transmission face being provided with an antireflective coating to reduce transmission losses.

In a preferred embodiment the optical folding system comprises at least two prisms, wherein each prism is configured to fold the principal optical axis through an angle of approximately 180°. The principal optical axis is thus folded into three substantially parallel parts. This reduces the length of the cell to one third of its unfolded length, thereby enhancing the advantages mentioned above.

The multipass spectroscopic absorption cell may comprise a White cell wherein the first reflector is a front mirror and the second reflector comprises first and second back mirrors.

Alternatively, the multipass spectroscopic absorption cell may comprise a Herriott cell wherein the first reflector is a first curved mirror and the second reflector comprises a second curved mirror.

The multipass spectroscopic absorption cell includes a measuring chamber that contains a sample gas. The measuring chamber preferably includes at least one window for entry and/or exit of the beam of light to or from the measuring chamber.

Advantageously, the multipass spectroscopic absorption cell has an interaction path length in the range 1 m-2000 m, preferably 4 m-500 m.

Advantageously, the first and second reflectors are configured to reflect the beam of light multiple times through the sample volume without overlapping itself, to maximise the sensitivity of the device.

According to another embodiment of the invention there is provided an optical absorption spectrometer including a multipass spectroscopic absorption cell according to any one of the preceding statements of invention, a light source configured to direct a beam of light into the measuring chamber and a detector configured to detect light exiting the measuring chamber.

Advantageously, the light source is a continuous broadband light source. The light source is preferably an incoherent and continually illuminated light source (such as a Xenon arc lamp, a deuterium lamp, an incandescent lamp or an LED).

Advantageously, the light detector is configured to analyse the spectrum of the detected light. Preferably, the detector is configured for detecting an optical absorption spectrum of light transmitted from the source through the sample volume. The light detector may for example be a Czerny-Turner spectrometer equipped with an imaging light detector (such as a CCD).

In a preferred embodiment, the invention provides the benefit of improving the rigidity of the cell and thereby making optical alignment more straightforward, and/or improving the detection sensitivity by increasing the length of the optical path along which the light interacts with the gas (i.e. the interaction path length). The invention is of particular relevance to multiple pass spectrometers which operate in the UV and visible ranges of the optical spectrum.

Accordingly, in one non-limiting embodiment of the present invention there is provided optical folding means, said folding means comprising optical elements configured to fold the optical axis of the cell by 180 degrees, and to translate the optical axis by a predetermined distance. Preferably the folding means is incorporated into a multipass optical cell.

Advantageously, the folding means is in the form of prisms used in total internal reflection. The prisms are preferably configured to allow folding of all light rays incident on the prisms. It is preferable for each folding means to be coated to reduce optical losses.

Alternative prism designs may be used to perform the same function. Alternative optical materials may be used for the prisms.

The folding means may be either a single folding means, or alternatively a plurality of folding means used in sequence. Each of the plurality may be of the same design or of different design in order to optimise the optical system design.

In a second non-limiting embodiment of the present invention there is provided an instrument comprising a multipass optical cell incorporating optical folding means, said folding means comprising optical elements configured to fold the optical axis of the cell by 180 degrees, and to translate the optical axis by a predetermined distance.

Advantageously, the instrument contains a folding means in the form of prisms used in total internal reflection. The prisms are preferably of dimension to allow folding of all light rays incident on the prisms. It is preferable for each folding means to be coated to reduce optical losses.

Alternative prism designs may be used to perform the same function. Alternative optical materials may be used for the prisms.

The instrument may incorporate either a single folding means, or alternatively a plurality of folding means used in sequence. Each of the plurality may be of the same design or of different design in order to optimise the optical system design.

The instrument may incorporate all mounting means for the folding means, including all adjustments thereto.

BRIEF DESCRIPTION OF THE FIGURES

Various embodiments of the invention will now be described by way of example with reference to the accompanying drawings, wherein.

DETAILED DESCRIPTION

Figure 1:
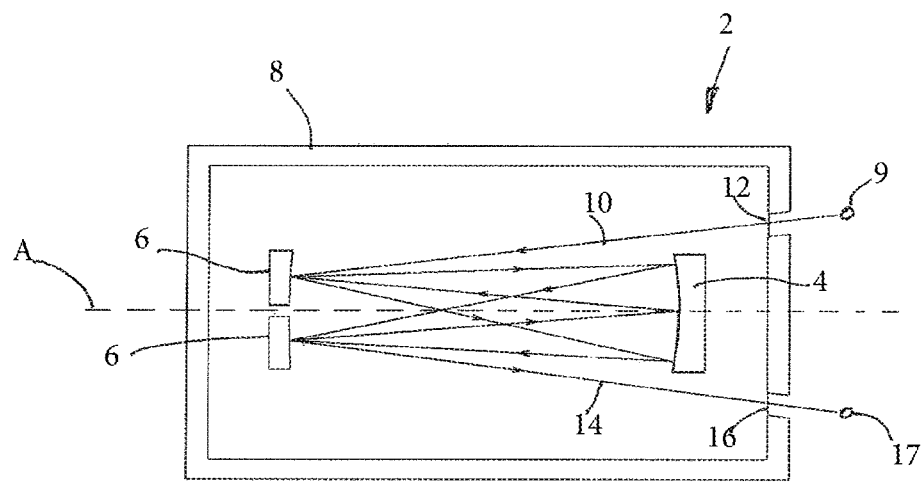
FIG. 1 shows a conventional White cell.

The optical arrangement of a conventional White cell 2 is illustrated schematically in FIG. 1. The White cell 2 consists of three concave mirrors of identical radius of curvature: a front (or field) mirror 4, which faces two side-by-side back (or objective) mirrors 6. The principal optical axis A of the White cell passes radially through the centre of the front mirror 4. The mirrors 4,6 are mounted within a measuring chamber 8, defining a sample volume V that contains a sample gas. The distance between the front and back mirrors 4,6 is typically approximately 80 cm, although larger and smaller instruments can also be designed.

A light source 9, for example a Xenon arc lamp, provides an input beam of light 10 that enters the measuring chamber 8 through an entrance window 12. Preferably, the light source 9 is a broadband source providing light in the ultraviolet (UV) or ultraviolet-visible (UV-Vis) spectral regions, although it may alternatively be an infrared (IR) source. The light is reflected a number of times between the mirrors 4,6 and finally an output beam 14 exits the measuring chamber 8 through an exit window 16, where it is detected by a suitable detector 17.

The detector 17 may for example be a CCD detector with an associated diffraction grating (not shown) that selects the wavelengths of light sensed by the detector. This light is then analysed by a spectrograph to detect the optical absorption spectra of the gas through which the light has passed.

The distance between the front mirror 4 and the two back mirrors 6 is twice the focal length of the mirrors, so that light from the source 9 is repeatedly refocused on the front mirror 4. In this example, the light traverses the chamber 8 eight times, providing a path length that is eight times the distance between the front and back mirrors. The number of passes can be controlled by adjusting the angular position of one of the back mirrors 6.

Figure 2:
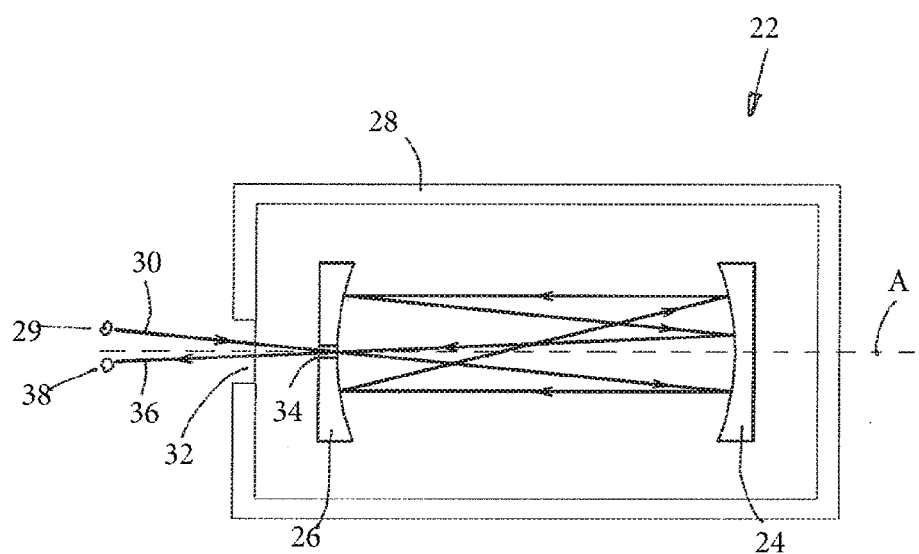
FIG. 2 shows a conventional Herriott cell.

The optical arrangement of a conventional Herriott cell 22 is illustrated schematically in FIG. 2. The Herriott cell 22 consists of two concave mirrors 24,26 of identical radius of curvature that are mounted facing each other. The principal optical axis A of the Herriott cell passes radially through the centres of the mirrors 24,26. The mirrors 24,26 are mounted within a measuring chamber 28, defining a sample volume V that contains a sample gas.

A light source 29 provides an input beam of light 30 that enters the measuring chamber 28 through a window 32. The light passes through an off-centre aperture 34 in the second mirror 26 and is reflected a number of times around the perimeters of the mirrors 24,26. Finally, an output beam 36 passes through the aperture 34 and exits the measuring chamber 28 through the window 32 where it is detected by a detector 38. Alternatively, the cell can be modified to allow the output beam 36 to pass through another aperture in the first mirror 24 and exit the measuring chamber 28 through an exit window at the opposite end of the chamber.

The distance between the two mirrors 24,26 may be adjusted to control the number of times the light traverses the chamber 8. In this example the light traverses the chamber six times, providing a path length that is six times the distance between the mirrors.

Figure 3:
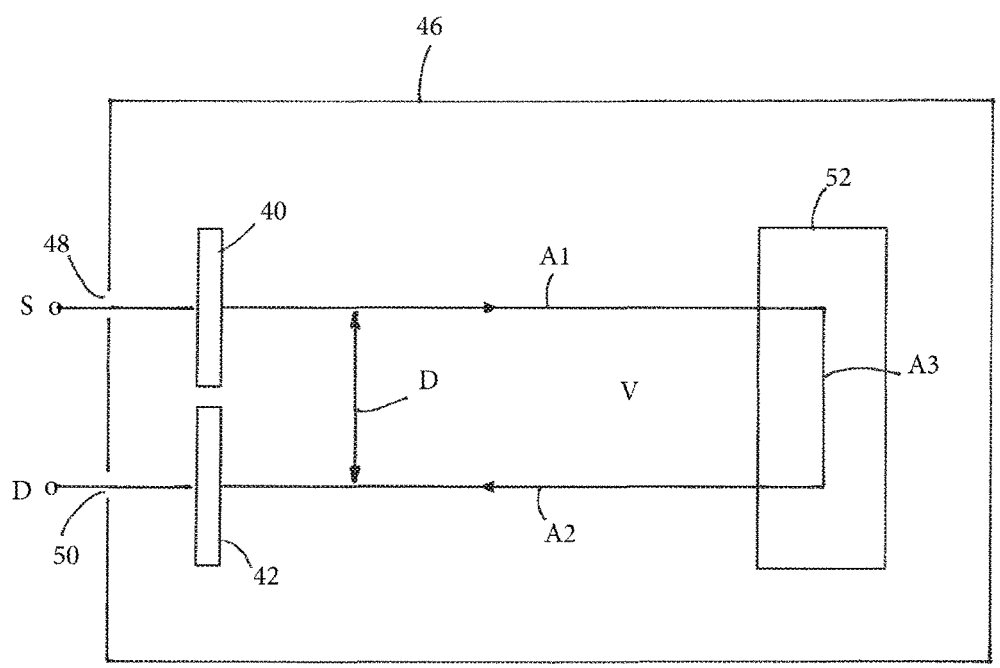
FIG. 3 illustrates a generic form of the invention.

According to the present invention a conventional multipass cell, for example a White cell or a Herriott cell, is modified by incorporating an optical folding system comprising one or more optical elements that fold the principal optical axis A of the cell. This is illustrated generically in FIG. 3, which shows the general scope of the invention. In this example, the first and second reflective elements 40,42 represent the mirrors that would normally be used in a multipass cell of conventional design to reflect a beam of light (here represented by the principal or chief optical ray 44) multiple times through the sample volume. Thus, for a White cell the first reflective element 40 represents the front mirror (ref 4 in FIG. 1) and the second reflective element 42 represents the two back mirrors (ref 6 in FIG. 1). In a Herriott cell the first and second reflective elements 40,42 represent respectively the first and second mirrors (ref 24,26 in FIG. 2).

The first and second reflective elements 40,42 are mounted within a measuring chamber 46, which defines a sample volume V that contains a sample gas. A light source S provides an input beam of light that enters the measuring chamber 46 through an entrance window 48. The light is reflected a number of times between the reflective elements 40,42 and finally an output beam exits the measuring chamber 46 through an exit window 50, where it is detected by a suitable detector D. This light is then analysed by a spectrograph (not shown) to detect the optical absorption spectra of the gas through which the light has passed.

In each of the subsequent figures the measuring chamber 46 that defines the sample volume V, the source S, the detector D and the entrance and exit windows 48,50 have been omitted for clarity.

In the present invention, the optical arrangement of the conventional multipass cell is modified by incorporating an optical folding system 52 that folds the principal optical axis A of the cell. In the example shown in FIG. 3 the principal optical axis A is folded twice through an angle of 90° and comprises first and second parts A1, A2 that are parallel and displaced from one another by a distance D, and an intermediate part A3 that is perpendicular to the first and second parts.

Figure 4:
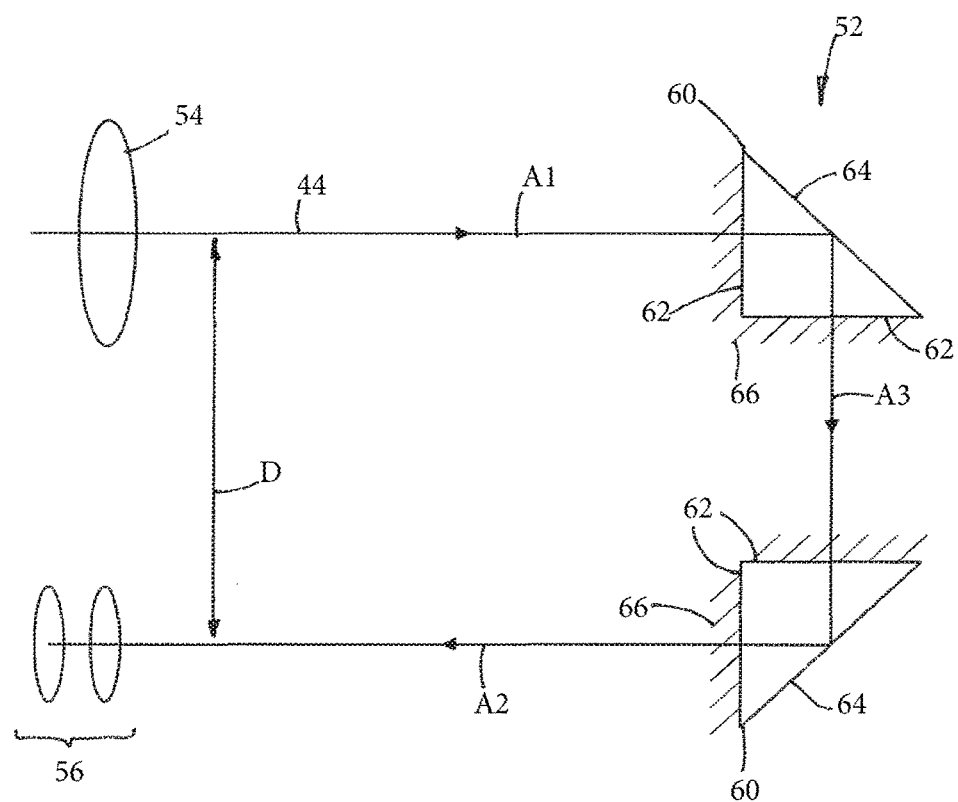
FIG. 4 illustrates a first embodiment of the invention based a White cell.

FIG. 4 shows schematically a modified White cell that includes an optical folding system 52. In the White cell the first reflective element comprises the large diameter front mirror 54, and the second reflective element comprises the two small diameter back mirrors 56. For simplicity the back mirrors 56 are shown axially displaced, although in practice they would be positioned side-by-side. In this example the optical folding system 52 comprises two right angle prisms 60. In this example each prism has two transmission faces 62 that are perpendicular to the principal optical axis A and a reflection face set at 45 degrees to the principal optical axis A (although any other convenient angle might be chosen). An anti-reflection coating 66 is provided on each the transmission faces 62.

In each prism 60 the principal optical ray 44 passes through the transmission faces and is totally internally reflected by the reflection face through an angle of 90°. The principal optical axis A thus comprises first and second parts A1, A2 that are parallel and displaced from one another by a distance D, and an intermediate part A3 that is perpendicular to the first and second parts. The principal optical axis A is folded through a total angle of 180°. The optical folding system 52 shown in FIG. 4 may also be used with other types of multipass cell, including for example the Herriott cell.

Figure 5:
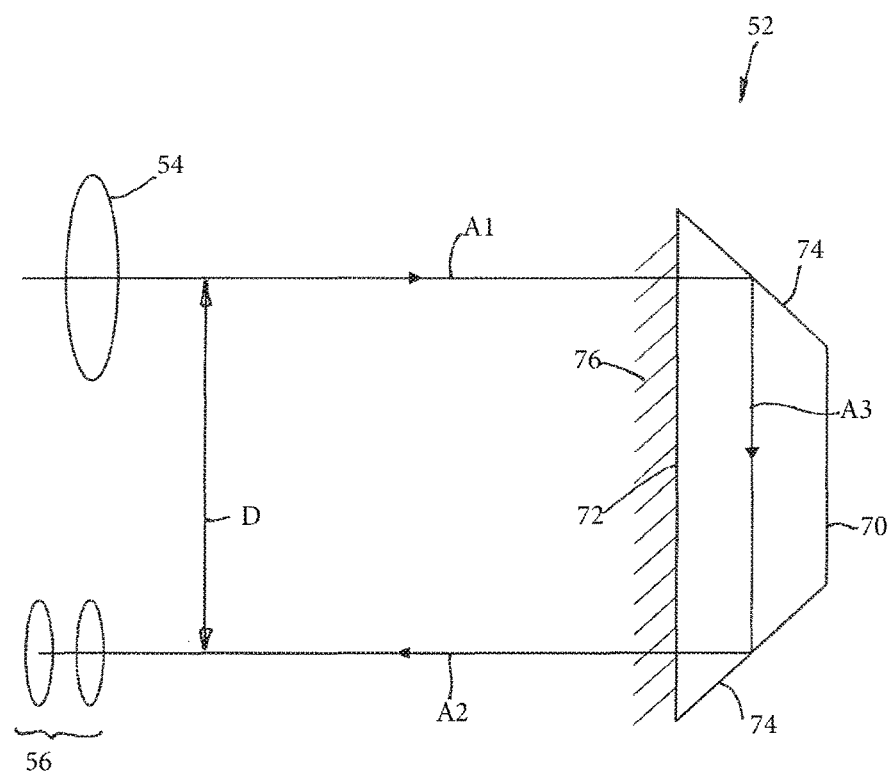
FIG. 5 illustrates a second embodiment of the invention based a White cell.

FIG. 5 shows schematically a modified White cell that incorporates a Porro prism 70 as the optical folding system 52. The White cell again includes a large diameter front mirror 54 and two small diameter back mirrors 56. The Porro prism 70 has the shape of a trapezium and comprises a transmission face 72 that is perpendicular to the principal optical axis and two reflection faces 74, each set at 45 degrees to the principal optical axis (although any other convenient angle might be chosen). An anti-reflection coating 76 is provided on the transmission face 72.

The principal optical ray 44 passes through the transmission face 72 and is totally internally reflected at each the reflection face 74 through an angle of 90°. The principal optical axis thus comprises first and second parts A1, A2 that are parallel and displaced from one another by a distance D, and an intermediate part A3 that is perpendicular to the first and second parts. As in the previous example, the principal optical axis A is thus folded through a total angle of 180°. The optical folding system 52 shown in FIG. 5 may also be used with other types of multipass cell, including for example the Herriott cell.

Figure 6:
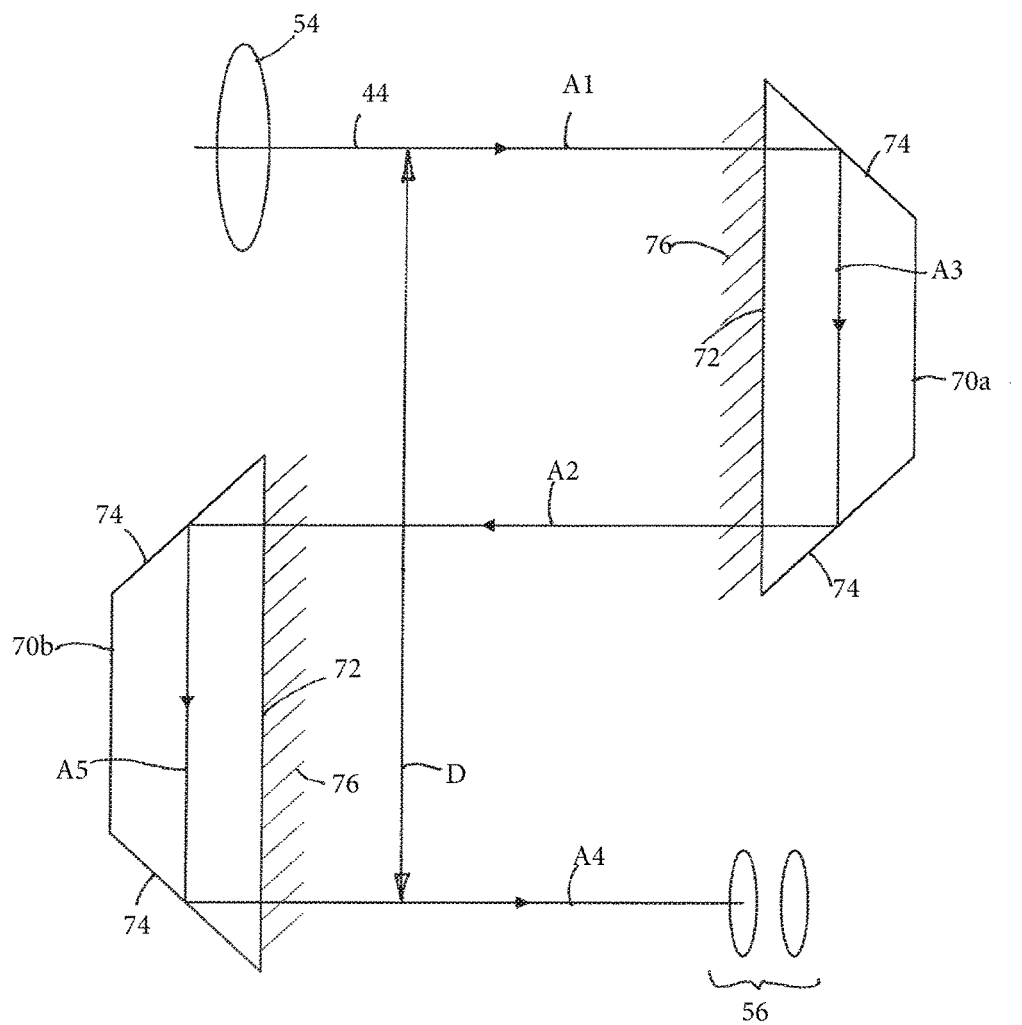
FIG. 6 illustrates a third embodiment of the invention based a White cell.

FIG. 6 shows schematically a modified White cell that incorporates two Porro prisms 70a,70b as the optical folding system 52. The White cell again includes a large diameter front mirror 54 comprising the first reflective element and two small diameter back mirrors 56 together comprising the second reflective element. Each Porro prism 70a,70b has the cross-sectional shape of a regular trapezium and comprises a transmission face 72 that is perpendicular to the principal optical axis and two reflection faces 74, each set at 45 degrees to the principal optical axis (although any other convenient angle might be chosen). An anti-reflection coating 76 is provided on the transmission face 72.

At each Porro prism 70a,70b the principal optical ray 44 passes through the transmission face 72 and is totally internally reflected at each the reflection face 74 through an angle of 90°. The principal optical axis A thus comprises first, second and third parts A1, A2, A4 that are all parallel, and two intermediate parts A3, A5 that are perpendicular to the first, second and third parts. The principal optical axis A is thus folded twice through an angle of 180°, the last part of the optical axis A4 being displaced from the first part A1 by a distance D. The optical folding system 52 shown in FIG. 6 may also be used with other types of multipass cell, including for example the Herriott cell.

It should be understood that the three parallel parts A1, A2, A4 of the principal optical axis need not necessarily lie in the same plane. For example, by rotating the second prism 70b through 120° about the second part A2 of the principal optical axis the third part A4 of the principal optical axis may be positioned equidistant from the first and second parts A1, A2 of the principal optical axis, thus providing a more compact arrangement.

Figure 7:
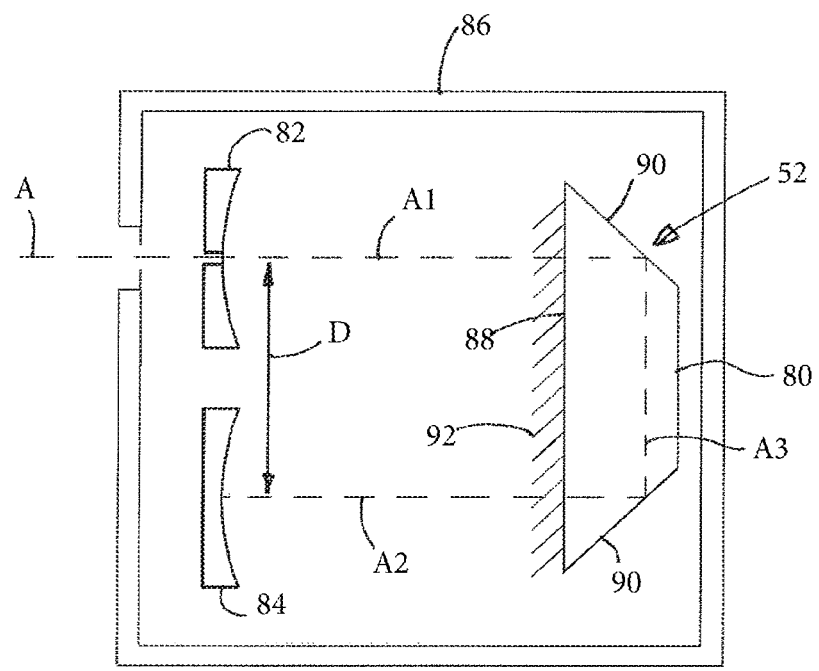
FIG. 7 illustrates a fourth embodiment of the invention based a Herriott cell.

FIG. 7 shows schematically a modified Herriott cell that incorporates a Porro prisms 80 as the optical folding system 52. The Herriott cell 22 includes of two concave mirrors 82,84 of identical radius of curvature that are mounted facing each other. The principal optical axis A of the Herriott cell passes radially through the centres of the mirrors 82,84. The mirrors 82,84 are mounted within a measuring chamber 86, defining a sample volume that contains a sample gas.

The Porro prism 80 has the cross-sectional shape of a regular trapezium and comprises a transmission face 88 that is perpendicular to the principal optical axis A and two reflection faces 90, each set at 45 degrees to the principal optical axis A (although any other convenient angle might be chosen). An anti-reflection coating 92 is provided on the transmission face 88.

A principal optical ray that passes through the transmission face 88 in the direction of the optical axis A will be totally internally reflected at each reflection face 90 through an angle of 90°. The principal optical axis thus comprises first and second parts A1, A2 that are parallel and displaced from one another by a distance D, and an intermediate part A3 that is perpendicular to the first and second parts. As in the previous example, the principal optical axis A is thus folded through a total angle of 180°. In use, the path of light through the Herriott cell will be similar to that described above with reference to FIG. 2, except of course that the light path will be folded by the optical folding system 52 comprising the Porro prism 80. For use in a UV multipass cell, the embodiment shown in FIG. 5 is usually preferred. In this case, the prism 70 is made of UV-grade fused silica. The antireflection coating 76 is typically a quarter wavelength coating of magnesium fluoride optimised at a wavelength around the centre of the sensitive range of the detector. Alternatively a multilayer coating can be used which reduces reflection loss from the coated surface as compared with a single layer coating. Incorporating such a prism requires a consideration of the adjustment sensitivity of the prism. To the first order, such a prism is insensitive to adjustment. In the plane of the FIG. 6, the optical rays are always deviated by 180 degrees. However, the other alignment angles are likewise insensitive, since they are at a minimum of a simple geometric identity—either cosine or sine—which are insensitive to small angles. Thus, adding such a prism does not add any additional difficulties in optical alignment of the multipass cell.

The above examples describe the use of both mirrors and prisms in the optical folding system. The choice of folding optics depends on the region of the optical spectrum, to reduce optical losses inside the multipass cell.

As a non-limiting example, some preferred optics are as follows:

| Spectral region | Folding method | Material |
| --- | --- | --- |
| UV | Prisms | Fused silica |
| Visible | Prisms | BK7 prism |

Certain examples will now be described to illustrate the advantages provided by the invention.

EXAMPLE 1

A conventional White cell has a distance between the front and back mirrors of 600 mm. The cell has the mirrors adjusted for 36 optical passes. Typically, the mirrors need to be adjusted to an accuracy of about 100 microradians and this adjustment needs to be maintained throughout the life of the instrument. The mirror position must remain stable under vibration, shock and large transitions in temperature.

This stability requirement is difficult to maintain. The mechanical design of a White Cell is typically tubular, where the supporting tube is perhaps 60 mm in diameter. The mirrors are mounted on the ends of the tube. Thus the mirror alignment depends on the mechanical strength and stability of the tube, which in this case is 600 mm long and 60 mm in diameter. This results in a limiting factor in maintaining optical alignment.

The key reason for this is that the flexibility of a simple structure such as a tube is proportional to the length cubed, and varies inversely as the second moment of the area:

$$X = ML^3/3EI, \text{ or as a figure of merit } X/M = L^3/3EI$$

Where X is the deflection, M is the applied force, L is the length, E is the modulus of elasticity and I is the second moment of area.

A typical White cell design might have a supporting tube 600 mm long, 60 mm outer diameter, with a wall thickness of 2 mm. The material is typically steel.

Thus X/M=2.25 um per Newton. This adversely degrades the optical alignment for relatively small deflection forces.

However, if we use two Porro prisms as in the fourth embodiment shown in FIG. 6 to reduce the mechanical length by a factor of three, the strength of the structure increases dramatically. In this case we get a factor 27 increase in strength by reducing L by a factor of three. In addition, the structure is wider. Although the move from a circular tube cross section to a different structure is not straightforward, we might reasonably expect a further increase in strength by a factor of 20 to 30, since the second moment of area generally goes as the dimension cubed.

Thus by incorporating path folding, we have improved the structural strength by a factor of about 27×20=540 times.

This reduces the deflection per unit force from 2.25 um per Newton to 4 nm per Newton, which does not significantly affect the optical alignment of the apparatus in normal use.

EXAMPLE 2

The sensitivity of a White cell, or indeed any multipath spectrometer, is proportional to the length of the cell. Thus there is a design goal to increase the length as much as possible. This gives rise to a design conflict. As explained in Example 1, there is a powerful disincentive to increasing the length of the tube since this makes the instrument very susceptible to shock, vibration and temperature changes.

However, we find that we can increase the effective length of a cell by incorporating prisms to fold the optical path.

In a cell of nominal length 600 mm, incorporating two Porro prisms increases the optical length of the cell and the interaction path length by a factor of three without increasing the mechanical length of the cell. This improves the detection limit by a factor of three.

We also achieve an improvement in structural strength, since the structure is wider, and hence has a higher second moment of area. Again this is difficult to estimate, but a reasonable and conservative estimate might be a 20 to 30 times improvement in mechanical rigidity.

The invention claimed is:

1. A multipass spectroscopic absorption cell comprising:
   a measuring chamber having a sample volume for receiving a sample gas to be measured,
   at least a first reflector and a second reflector that are configured to reflect a beam of light multiple times through the sample volume, at least one of said first and second reflectors defining a principal optical axis that extends through the sample volume, and
   an optical folding system located on the principal optical axis between the first and second reflectors and within the measuring chamber, wherein said optical folding system comprises one or more prisms and is configured to fold the principal optical axis through an angle greater than 0°;

wherein the principal optical axis includes a first part extending between the first reflector and the optical folding system, and a second part extending between the second reflector and the optical folding system, wherein the first part is parallel to the second part, and wherein the first reflector and the second reflector are configured to reflect the beam of light multiple times through the optical folding system.

2. A multipass spectroscopic absorption cell according to claim 1, wherein the optical folding system is configured to fold the principal optical axis at least once through an angle of approximately 180°.

3. A multipass spectroscopic absorption cell according to claim 2, wherein the optical folding system is configured to fold the principal optical axis twice through an angle of approximately 180°.

4. A multipass spectroscopic absorption cell according to claim 2, wherein the folded principal optical axis comprises a first part on a first side of the optical folding system and a second part on a second side of the optical folding system, wherein the optical folding system is configured to displace the first part from the second part by a displacement distance D, where D is greater than 0.

5. A multipass spectroscopic absorption cell according to claim 1, wherein each prism is made of a low loss material to provide a transmission loss of less than 1% with the chosen light.

6. A multipass spectroscopic absorption cell according to claim 1, wherein the absorption cell is configured for use with visible light and each said prism comprises BK7 prism, or wherein the absorption cell is configured for use with ultraviolet light and each said prism comprises a fused silica prism.

7. A multipass spectroscopic absorption cell according to claim 1, wherein each prism includes at least one transmission face and at least one reflection face, and wherein the at least one transmission face is provided with an antireflective coating.

8. A multipass spectroscopic absorption cell according to claim 1, wherein the optical folding system comprises at least two prisms, wherein each said prism is configured to fold the principal optical axis through an angle of approximately 90°.

9. A multipass spectroscopic absorption cell according to claim 1, wherein the optical folding system comprises at least one prism that is configured to fold the principal optical axis through an angle of approximately 180°.

10. A multipass spectroscopic absorption cell according to claim 9, wherein the optical folding system comprises at least two prisms, wherein each prism is configured to fold the principal optical axis through an angle of approximately 180°.

11. A multipass spectroscopic absorption cell according to claim 1, comprising a White cell wherein the first reflector is a front mirror and the second reflector comprises first and second back mirrors.

12. A multipass spectroscopic absorption cell according to claim 1, comprising a Herriott cell wherein the first reflector is a first curved mirror and the second reflector comprises a second curved mirror.

13. A multipass spectroscopic absorption cell according to claim 1, wherein the measuring chamber includes at least one window for entry and/or exit of the beam of light to or from the measuring chamber.

14. A multipass spectroscopic absorption cell according to claim 1, having an interaction path length in the range 1 m-2000 m.

15. A multipass spectroscopic absorption cell according to claim 14, having an interaction path length in the range 4 m-500 m.

16. A multipass spectroscopic absorption cell according to claim 1, wherein the first and second reflectors are configured to reflect the beam of light multiple times through the sample volume without overlapping itself.

17. An optical absorption spectrometer including:
a multipass spectroscopic absorption cell comprising:
    a measuring chamber having a sample volume for receiving a sample gas to be measured,
    at least a first reflector and a second reflector that are configured to reflect a beam of light multiple times through the sample volume,
    at least one of said first and second reflectors defining a principal optical axis that extends through the sample volume, and
    an optical folding system located on the principal optical axis between the first and second reflectors and within the measuring chamber, wherein said optical folding system comprises one or more prisms and is configured to fold the principal optical axis through an angle greater than 0°, wherein the principal optical axis includes a first part extending between the first reflector and the optical folding system, and a second part extending between the second reflector and the optical folding system, wherein the first part is parallel to the second part within the measuring chamber;
a light source configured to direct a beam of light into the measuring chamber; and
a detector configured to detect light exiting the measuring chamber;
    wherein the first reflector and the second reflector are configured to reflect the beam of light multiple times through the optical folding system.

18. An optical absorption spectrometer according to claim 17, wherein the light source is a continuous broadband light source.

19. An optical absorption spectrometer according to claim 17, wherein the light detector is configured to analyze the spectrum of the detected light.

20. An optical absorption spectrometer according to claim 19, wherein the detector is configured for detecting an optical absorption spectrum of light transmitted from the source through the sample volume.

* * * * *